United States Patent
Woodward et al.

(10) Patent No.: US 11,801,157 B2
(45) Date of Patent: Oct. 31, 2023

(54) OSTOMY DEVICE

(71) Applicant: Advanced Medical Solutions Limited, Winsford (GB)

(72) Inventors: Roxanna Woodward, Chester (GB); Wayne Bonnefin, Chester (GB)

(73) Assignee: Advanced Medical Solutions Limited, Cheshire (GB)

( * ) Notice: Subject to any disclaimer, the term of this patent is extended or adjusted under 35 U.S.C. 154(b) by 585 days.

(21) Appl. No.: 16/657,764

(22) Filed: Oct. 18, 2019

(65) Prior Publication Data
US 2020/0121490 A1 Apr. 23, 2020

(30) Foreign Application Priority Data
Oct. 19, 2018 (GB) .................................. 1817097

(51) Int. Cl.
*A61F 5/443* (2006.01)
*A61F 5/44* (2006.01)
*A61L 24/00* (2006.01)
*A61L 24/08* (2006.01)

(52) U.S. Cl.
CPC ............ *A61F 5/443* (2013.01); *A61F 5/4404* (2013.01); *A61L 24/0031* (2013.01); *A61L 24/08* (2013.01); *A61L 2400/14* (2013.01)

(58) Field of Classification Search
CPC .... A61F 5/443; A61F 5/4404; A61L 24/0031; A61L 24/08; A61L 2400/14
See application file for complete search history.

(56) References Cited

U.S. PATENT DOCUMENTS

| | | | |
|---|---|---|---|
| 4,062,361 A | | 12/1977 | Poulsen |
| 4,376,799 A | * | 3/1983 | Tusim ..................... B32B 27/08 604/339 |
| 4,755,177 A | | 7/1988 | Hill |
| 5,593,397 A | * | 1/1997 | La Gro ................... A61F 5/443 604/355 |
| 5,722,965 A | * | 3/1998 | Kuczynski .............. A61F 5/443 604/338 |
| 5,730,736 A | * | 3/1998 | Sawers ............... A61F 13/0226 604/336 |
| 6,454,740 B1 | * | 9/2002 | Mody ................ A61M 25/0097 604/95.04 |
| 6,455,161 B1 | * | 9/2002 | Regnier ..................... C08J 5/18 428/483 |

(Continued)

FOREIGN PATENT DOCUMENTS

| | | |
|---|---|---|
| EP | 0753290 A2 | 1/1997 |
| EP | 0832626 B2 | 6/2006 |

(Continued)

OTHER PUBLICATIONS

United Kingdom Patent Office Search Report for Application No. 1817097.7, dated Mar. 28, 2019 (4 pages).

(Continued)

*Primary Examiner* — Guy K Townsend
(74) *Attorney, Agent, or Firm* — Michael Best & Friedrich LLP (57) ABSTRACT

The present invention relates to an ostomy device for contacting a stoma. The present invention also relates to the use of an ostomy device for contacting a stoma and a kit of parts for preparing an ostomy assembly or system.

20 Claims, 2 Drawing Sheets

(56) References Cited

U.S. PATENT DOCUMENTS

| | | | | |
|---|---|---|---|---|
| 6,559,234 | B1* | 5/2003 | Arai | C08J 9/06 |
| | | | | 526/170 |
| 6,579,271 | B1* | 6/2003 | Aruffo | A61F 17/00 |
| | | | | 206/440 |
| 7,270,860 | B2* | 9/2007 | Giori | B32B 27/32 |
| | | | | 428/34.1 |
| 7,807,241 | B2* | 10/2010 | Sasagawa | B32B 25/04 |
| | | | | 428/36.1 |
| 7,993,739 | B2* | 8/2011 | Barger | B32B 5/18 |
| | | | | 428/318.6 |
| 9,895,255 | B2* | 2/2018 | Chang | B32B 27/34 |
| 10,322,024 | B2* | 6/2019 | Chang | B32B 27/08 |
| 10,470,917 | B2* | 11/2019 | Chang | B32B 27/32 |
| 10,980,661 | B2* | 4/2021 | Chang | B32B 27/065 |
| 11,351,054 | B2* | 6/2022 | Chang | B32B 5/32 |
| 2002/0025394 | A1* | 2/2002 | Bradfute | B32B 27/30 |
| | | | | 428/476.1 |
| 2003/0004477 | A1* | 1/2003 | Nielsen | A61F 5/448 |
| | | | | 604/336 |
| 2007/0005032 | A1* | 1/2007 | Shan | A61F 5/448 |
| | | | | 604/342 |
| 2007/0237916 | A1* | 10/2007 | Rasmussen | A61F 5/441 |
| | | | | 428/521 |
| 2010/0210745 | A1* | 8/2010 | McDaniel | C09D 7/48 |
| | | | | 521/55 |
| 2010/0324511 | A1* | 12/2010 | Dove | A61F 5/445 |
| | | | | 604/338 |
| 2010/0330356 | A1* | 12/2010 | Jokisch | B32B 27/065 |
| | | | | 428/317.1 |
| 2011/0172619 | A1 | 7/2011 | Argent | |
| 2011/0230850 | A1* | 9/2011 | Stroebech | A61L 24/06 |
| | | | | 604/344 |
| 2011/0250626 | A1* | 10/2011 | Williams | C12Q 1/34 |
| | | | | 106/4 |
| 2012/0010580 | A1* | 1/2012 | Forbes | A61F 5/441 |
| | | | | 604/338 |
| 2012/0143155 | A1* | 6/2012 | Edvardsen | A61F 5/443 |
| | | | | 604/318 |
| 2012/0232504 | A1* | 9/2012 | Chang | A61F 5/445 |
| | | | | 428/476.1 |
| 2013/0310782 | A1* | 11/2013 | Chang | B32B 27/308 |
| | | | | 604/333 |
| 2014/0205828 | A1* | 7/2014 | Chang | B32B 27/304 |
| | | | | 428/317.1 |
| 2014/0207094 | A1* | 7/2014 | Chang | B32B 27/302 |
| | | | | 604/339 |
| 2014/0221950 | A1* | 8/2014 | Chang | A61L 28/0026 |
| | | | | 252/62 |
| 2014/0221951 | A1* | 8/2014 | Chang | A61F 5/445 |
| | | | | 604/332 |
| 2014/0371698 | A1* | 12/2014 | Chang | B32B 27/12 |
| | | | | 181/294 |
| 2016/0151197 | A1* | 6/2016 | Johnsen | A61F 13/0246 |
| | | | | 428/40.1 |
| 2017/0042722 | A1* | 2/2017 | Chang | B32B 7/12 |
| 2018/0125696 | A1* | 5/2018 | Chang | B32B 27/306 |
| 2019/0231581 | A1* | 8/2019 | Chang | B32B 5/32 |

FOREIGN PATENT DOCUMENTS

| | | | | |
|---|---|---|---|---|
| EP | 2108345 A1 | 10/2009 | | |
| WO | 2012/022354 A1 | 2/2012 | | |
| WO | WO-2012022354 A1 * | 2/2012 | | A61F 5/443 |
| WO | WO-2016162038 A1 * | 10/2016 | | A61F 5/443 |

OTHER PUBLICATIONS

European Patent Office Extended Search Report for Application No. 19204187.9 dated Mar. 20, 2020 (9 pages).

European Patent Office Action for Application No. 19204187.9 dated Feb. 15, 2023 (6 pages).

* cited by examiner

OSTOMY DEVICE

CROSS-REFERENCE TO RELATED APPLICATION

This patent application claims priority to United Kingdom Patent Application No. 1817097.7, filed Oct. 19, 2018, the entire content of which is hereby incorporated by reference.

FIELD OF THE INVENTION

The present invention relates to an ostomy device for contacting a stoma. The present invention also relates to the use of an ostomy device for contacting a stoma and a kit of parts for preparing an ostomy assembly or system.

BACKGROUND OF THE INVENTION

Bowel related diseases, such as Crohn's disease, Ulcerative Colitis or Bowel Cancer, can lead to a patient requiring ostomy surgery. The surgery involves a procedure of creating a stoma, which diverts the intestinal tract out through an opening in the abdomen of the patient's body, away from the rectum or bladder and into a collection pouch, thus allowing a portion of the bowel to heal. Stomas are often reversible, depending on nature of the condition being treated, and their location may vary in accordance with the diseased area of the intestinal tract or, even, the urinary tract. Typically, ostomy patients will require an ostomy device to collect stoma output passing out from the body through the stoma. These devices essentially comprise a collection pouch for collecting ostomy output (also referred to as effluent) as well as an adhesive barrier (also known as a wafer or skin barrier). The adhesive barrier is responsible for securing the collection pouch to the user via an area of peristomal skin surrounding the stoma. The adhesive barrier also serves to protect the peristomal skin from output leaking from the end of the stoma. The stoma output can cause the user discomfort when coming into contact with the peristomal skin due to the output containing enzymes (e.g. proteases, lipases, etc.) which can break down the user's skin leading to irritation. For this reason, it is important that ostomy devices are able to conform to the perimeter and anatomy of a given stoma in order to provide protection for the peristomal skin from the output leaking from the stoma.

Individuals of any age, but with a minimum weight of 2.5 kilograms, can undergo ostomy surgery. Surgeons performing ostomy surgery aim to create a stoma which protrudes from the abdomen and is circular in shape such that the stoma output falls directly into a collection pouch secured to a user without leakage. This, however, is not always achievable. In addition to the difficulties in surgically creating a stoma, it will be appreciated that stomas may vary in size and shape depending on the profile of the user and the skill of the surgeon. Therefore, it can be difficult for the user to obtain an adhesive barrier which forms a good fit with its stoma. Examples of adhesive barriers known in the art include so called, cut-to-fit, pre-cut and mouldable barriers.

Cut-to-fit barriers tend to require the user to place a template sizing guide against the stoma to provide an estimate of the stoma dimensions before then using the sizing guide to mark out and cut the adhesive barrier from a rigid base plate or sheet. With this option, the user is required to check the fit of the cut adhesive barrier against the stoma and, if the size and fit is not suitable, repeat the cut-to-fit process until a desirable fit is achieved. If the adhesive barrier is cut larger than the stoma, the patient will have exposed skin around the stoma and will therefore be at risk of effluent leaking and damaging the peristomal skin.

Pre-cut barriers are barriers that have been cut to a predetermined shape and size by the manufacturer, and users are required to select a product which best fits the dimensions of their stoma. Inevitably, this option suffers from the drawbacks that the stoma may not be of a shape or dimension that provides a good fit with the pre-cut barrier. Stomas are also susceptible to changes in their dimensions, particularly after surgery, and, therefore, a pre-cut barrier which once formed a good fit with a stoma may become poorly fitting and unusable over time.

More recently, mouldable ostomy devices have emerged to provide the user with versatile adhesive barrier components capable of moulding to suit the size of a given stoma. Reference is made to US2016/0151197A1 and U.S. Pat. No. 6,840,924, both of which describe a mouldable adhesive barrier technology which provides a "roll-back" adhesive to form a tight seal around a stoma. The adhesive barrier consists of a relatively thick, resilient film layer sandwiched between two hydrocolloid layers and has an opening for a stoma. To use the device, the user must roll back the edges of the opening to increase its diameter so as to allow insertion of the stoma. Once the stoma is inserted into the opening, the edges of the opening are released to rebound and close the opening and contact around the edge of the stoma.

Despite the current mouldable ostomy technologies allowing users to have a more secure adhesive barrier to their stoma, they suffer from drawbacks. For example, many of the current technologies may be difficult for the user to apply and require the user to carefully roll back the inner edge of the adhesive barrier before then inserting the stoma into the opening. This can be difficult to perform and therefore may present a challenge for users with poor dexterity and can take the user a long time to apply to the stoma. In addition to this, it has also been found that a larger force is applied to the stoma by the relatively thick resilient barrier. This may cause discomfort due to a tighter fit being formed by the moulding mechanism. Furthermore, in order to achieve the current moulding mechanisms, the current devices require a complicated laminate structure having several layers of material. This is, of course, intricate to manufacture and also increases the thickness of the adhesive barrier which in turn can affect the breathability, conformability and durability of the devices.

It is an object of the present invention to obviate or mitigate one or more of the above mentioned disadvantages.

SUMMARY OF THE INVENTION

The present inventors have developed an ostomy device having a laminate structure for contacting a stoma. In general terms, the present inventors have developed an ostomy device having a laminate structure that is readily stretchable by a user to allow a stoma to be inserted into the device aperture, and which may then retract/contract to form a gentle contact around the stoma. The term contract and retract are used interchangeably herein.

In a first aspect of the present invention there is provided an ostomy device for contacting a stoma comprising a laminate structure, the laminate structure comprising a substrate layer and an adhesive layer, an aperture formed through the laminate structure and defined by a peripheral wall, wherein the peripheral wall is operable to (i) expand in the plane of the laminate structure from a pre-expanded state to an expanded state to radially enlarge the aperture to allow insertion of the stoma through the aperture and (ii) contact the stoma.

The device of the present invention has a peripheral wall that is able to expand in the plane of the device. This allows the user to radially enlarge the aperture, whereby the stoma may be readily inserted through the laminate structure. For instance, to apply the product to a stoma, the user may apply opposing stretching forces to the device either side of the aperture to cause radial expansion of the peripheral wall in the plane of the device. This would radially enlarge the aperture and allow insertion of the stoma (see the radial expansion/contraction arrows in FIG. 4). In embodiments, the user may perform this with a single stretching movement, e.g. manually, such as by hand. Advantageously, this mode of action does not require the user to roll or mould the peripheral wall, which would require greater dexterity and skill from the user. The radial expansion does not require the peripheral wall of the aperture to deviate from the plane of the device (i.e. no upward or downward movement away from the plane is required) which makes application of the device to the stoma less complex. It will be appreciated that reference to "in the plane" of the laminate structure as used herein means that radial expansion or contraction occurs in substantially the same plane as the laminate structure (i.e. where there is no significant deviation from the plane). In some embodiments, the peripheral wall is operable to expand (and/or contract/retract as the case may be) in the plane of the laminate structure without any deviation from the plane.

In further embodiments, once in its expanded state, the peripheral wall of the device may be further operable to contract (or retract) from the expanded state towards its pre-expanded state to radially reduce the aperture and contact the stoma with the peripheral wall. It will be appreciated that once stoma insertion has occurred, the moderate contraction of the peripheral wall back towards its pre-expanded or resting state (i.e. the state before stretching) enables a more gentle force being applied by the peripheral wall against the outer wall of the stoma when compared to certain prior art ostomy devices. This contact may also in embodiments form a secure "leak free" seal around the stoma. This may for instance be achieved by selecting a suitable laminate structure having material properties (such as thickness, elasticity, flexibility and/or resilience) which enable the peripheral wall to retract with a suitably low force so as to form a seal against the stomal skin but without causing damage to the stomal skin.

In embodiments, the contact between the peripheral wall and the stoma forms a seal between the peripheral wall and the stoma. By this, it is meant that the peripheral wall of the device may engage with an outer wall (i.e. perimeter or circumference) of a stoma. The contact between the peripheral wall and the stoma may form a seal with the outer wall of the stoma thus forming a protective barrier capable of preventing stoma output from coming into contact with the peristomal skin. The seal may be a fluid-tight seal. It will be appreciated that during use, output from the stoma may leak out from the stoma open end. This output can typically cause irritation to the user upon contact with the user's peristomal skin. By contacting the base of the stoma and forming a seal, the device can therefore reduce the risk of irritation caused to the user by stoma output as the peristomal skin is no longer exposed.

In some embodiments, when contacting the stoma, the device of the present invention conforms to the anatomy of the stoma to form a continuous seal with the base of the outer wall or profile of the stoma.

Laminate Structure

The ostomy device of the present invention comprises a laminate structure. The laminate structure of the devices of the invention comprise a substrate layer and an adhesive layer. It is contemplated that other layers may be present in the laminate structure. In some embodiments, the laminate structure may comprise a single substrate layer. In embodiments, the laminate structure may include a single adhesive layer. In some embodiments there may be multiple substrate layers and/or multiple adhesive layers. The laminate structure may include a single substrate layer and single adhesive layer. In further embodiments, the laminate structure does not include layers other than the substrate and adhesive layers. For instance, the laminate may consist of a single substrate layer and single adhesive layer.

Substrate Layer

In some embodiments, the substrate layer may include a polymer. The polymer may be selected from any material possessing performance characteristics suitable for protecting the peristomal skin against effluent when in use. Suitable polymers include materials which are conformable to the contours of a user's body. Suitable polymers may be one or more of moisture resistant, impermeable to bacteria and/or die-cuttable. Suitable polymers include, but are not necessarily limited to, polyurethane based polymers and polyethylene based polymers. A suitable example is MEDIFOL™ 3D perforated polyethylene film. The polymer may thus comprise polyurethane and polyethylene. The substrate layer may be formed of a single piece of material. It is also however intended that the term "substrate layer" include the situation where multiple pieces of material are integrated to form a substrate layer, e.g. where multiple pieces of material are laminated to form a substrate layer. In an embodiment, the term substrate layer refers to a single piece of material.

In some embodiments, the substrate layer of the present invention may include a foam and/or film. In some embodiments, the substrate layer may include a layer of foam laminated to a film. For example, a substrate layer may include a layer of foam laminated to a film backing. In a particular example, the substrate layer may comprise (e.g. consist of) a polyurethane foam laminated to a polyurethane film backing.

In embodiments, the device of the present invention does not contain a foam, e.g. a polymeric foam. In embodiments, the substrate layer does not contain a foam, e.g. a polymeric foam. It will also be appreciated that when the substrate layer does not contain a foam, the substrate layer may still include multiple pieces of material integrated to form the substrate layer but wherein the multiple pieces do not include a foam. The laminate may for instance be a polymeric film laminate, e.g. wherein both the substrate layer and adhesive layer are both polymeric films.

Adhesive Layer

In some embodiments, the adhesive layer may include a hydrocolloid, silicone adhesive, acrylic adhesive, polyurethane adhesive or any combination thereof. The adhesive layer may include any material which is suitable for adhering the device of the present invention to the body of a user. Examples of such materials include hydrocolloids.

In some preferred embodiments, the adhesive layer comprises, or optionally is, a hydrocolloid. In such embodiments, the hydrocolloid may include any material possessing gel-forming and/or elastomeric or adhesive properties and that may be applied to a suitable substrate to form a laminate structure. The hydrocolloid of the present invention may include a number of components. The hydrocolloid may include a blend of water soluble polymers (e.g. carboxymethylcellulose and/or pectin) together with suitable elastomers and/or adhesives. In some embodiments, the hydrocolloid may include carboxymethylcellulose, polysaccharides and pectin. Moreover, the hydrocolloid of the present invention may include any one of the ingredients specified in the embodiments described below, Table 1 b or a combination thereof in a suitable amount. When the adhesive layer of the present invention is a hydrocolloid, this has the advantage that, during use, output leaking from the stoma end and in the area of the stoma or peristomal skin may be absorbed into the hydrocolloid to form a gel.

In embodiments, the hydrocolloid may include a polybutylene, for example, polyisobutylene. The polybutylene may have a wt % (i.e. wt % of the overall hydrocolloid composition) of from about 20 wt % to about 30 wt % or from about 25 wt % to about 30 wt %. In particular, the hydrocolloid may include polyisobutylene having a wt % of from about 20 wt % to about 30 wt % or from about 25 wt % to about 30 wt %. The polyisobutylene may be approximately 28 wt %.

In other embodiments, the hydrocolloid may include water soluble polymers, for example, carboxymethylcellulose and/or pectin. The hydrocolloid may include such water soluble polymers in a wt % (i.e. wt % of the overall hydrocolloid composition) of from about 5 wt % to about 40 wt %, from about 10 wt % to about 40 wt %, from about 20 wt % to about 40 wt % or from about 30 wt % to about 40 wt %. In some embodiments, the hydrocolloid may include carboxymethylcellulose in an amount of from 20 wt % to about 40 wt % or from 30 wt % to about 40 wt %. In addition (or in the alternative), the hydrocolloid may include pectin at from about from about 5 wt % to about 10 wt %. Typically, the hydrocolloid may include carboxymethylcellulose at from 20 wt % to about 40 wt % and pectin at from about 5 wt % to about 10 wt %. Preferably, the hydrocolloid may include carboxymethylcellulose in an amount of from 30 wt % to about 40 wt % and pectin in an amount of from about 5 wt % to about 10 wt %. In one embodiment, the hydrocolloid may include carboxymethylcellulose at approximately 30 wt % and/or pectin at approximately 6 wt %.

In some embodiments, the hydrocolloid may include styrene based block copolymers, for example, poly(styrene-butadiene-styrene) block copolymers, poly(styrene-isoprene-styrene) block copolymers or poly(styrene-ethylene-butylene-styrene) block copolymers. The hydrocolloid may include such block copolymers having a wt % (i.e. wt % of the overall hydrocolloid composition) of from about 10 wt % to about 20 wt %, from about 15 wt % to about 20 wt %. Typically, the styrene based block copolymer may be a poly(styrene-butadiene-styrene) block copolymers at from about 15 wt % to about 20 wt %.

The hydrocolloid may also include a hydrocarbon resin, for instance, hydrocarbon resins comprising low molecular weight hydrocarbon polymers, for example Escorez™ type resins. The hydrocolloid may include such hydrocarbon resins having a wt % (i.e. wt % of the overall hydrocolloid composition) of from 5 wt % to about 20 wt %, from 10 wt % to about 20 wt % or from 5 wt % to about 15 wt %. Typically, the hydrocarbon resin is provided in the hydrocolloid an amount of approximately 10 wt %.

The hydrocolloid may also include a flocking powder, for instance, purified powered cellulose. The hydrocolloid may include such flocking materials having wt % (i.e. wt % of the overall hydrocolloid composition) of from about 5 wt % to about 20 wt %, from 10 wt % to about 20 wt % or from 5 wt % to about 15 wt %. Typically, the flocking powder is approximately 8 wt %.

The hydrocolloid may also include a preservative having wt % (i.e. wt % of the overall hydrocolloid composition) of from about 0.1 wt % to about 2 wt % or from 0.1 wt % to about 1 wt %. In some embodiments, hydrocolloid may include a mineral oil having wt % (i.e. wt % of the overall hydrocolloid composition) of from 0.01 wt % to about 1 wt %, from about 0.01 wt % to about 0.5 wt %, from about 0.01 wt % to about 0.1 wt %, or from about 0.01 wt % to about 0.05 wt %.

In some embodiments, the hydrocolloid may include polyisobutylene at from about 25 wt % to about 30 wt %, carboxymethylcellulose at from 30 wt % to about 40 wt %, pectin at from about 5 wt % to about 10 wt %, poly(styrene-butadiene-styrene) block copolymers at from about 15 wt % to about 20 wt %, a hydrocarbon resin at from 5 wt % to about 15 wt %, purified powered cellulose from 5 wt % to about 15 wt %, a preservative from 0.1 wt % to about 1 wt % and/or a mineral oil from 0.01 wt % to about 0.05 wt %. It will be appreciated that the relative amounts of the components may vary within the wt % ranges specified above but will not exceed a total of 100 wt % of the overall hydrocolloid when taken in combination.

Thickness of Layers

The laminate structure of the ostomy device of the present invention may in some embodiments have an overall thickness of from about 0.1 mm to about 10 mm, from about 0.1 mm to about 5 mm, from about 0.2 mm to about 5 mm, from about 0.1 mm to about 3 mm or from about 0.1 mm to about 1.0 mm or, even more preferably from about 0.5 mm to about 1.0 mm. Preferably, the laminate structure of the ostomy device of the present invention may have an overall thickness of from 0.6 mm to about 0.9 mm, from 0.6 mm to about 0.8 mm, or from 0.65 mm to about 0.75 mm. Suitably, the overall thickness of the laminate structure is preferably such that the laminate is flexible and conformable to the contours of the user's body. It is also preferred that the thickness of the laminate structure allows the device to be readily stretched by a user to expand the aperture. This has the advantage of providing a "stretch-fit" mechanism which allows the user to easily control stretching of the aperture formed within the device for insertion of a stoma, e.g. by hand. It will be appreciated that the thickness required to achieve the "stretch-fit" mechanism will depend on the laminate materials used (i.e. the substrate layer and adhesive layer).

Whilst the device of the present invention is capable of forming a "leak free" seal around the stoma when in use, it may do so whilst exerting a gentle rebound or contraction force against the outer wall of stoma, as compared to the prior art devices (e.g. US2016/0151197A1 and U.S. Pat. No. 6,840,924) thus providing the user with a comfortable but protective fit. In some embodiments, this may be achieved when the overall thickness of the laminate structure is from about 0.1 mm to about 1.0 mm or, even more preferably, from about 0.5 mm to about 1.0 mm.

In embodiments, the thickness of the substrate layer of the device of the present invention is from about 0.001 mm to about 0.1 mm, from about 0.005 mm to about 0.1 mm, from about 0.001 mm to about 0.05 mm or, preferably, from about 0.005 mm to about 0.05.

In further embodiments, the thickness of the adhesive layer of the device of the present invention is from about 0.1 mm to about 10 mm, from about 0.1 mm to about 5 mm or 0.1 mm to about 3.0 mm or, even more preferably from about 0.2 mm to about 4.0 mm or from about 0.5 mm to about 3.0 mm.

In embodiments the laminate structure of the device of the present invention has an extensibility of from about 1 N/cm to about 10 N/cm, from about 3 N/cm to about 8 N/cm, from about 4 N/cm to about 7 N/cm, from about 4.5 N/cm to about 6.5N/cm, from about 5 N/cm to about 6 N/cm or even from about 5 N/cm to about 5.5 N/cm.

The laminate structure of device of the present invention may have a permanent set (%) value of less than or equal to about 20%, or less than or equal to about 10%, or less than or equal to about 5%, or less than or equal to about 2%, or less than or equal to about 1.8%, or less than or equal to about 1.75%, or less than or equal to about 1.6%, or less than or equal to about 1.5%.

In embodiments, the substrate layer of the device of the present invention may have a moisture vapour transmission rate of at least about 500 $g/m^2/24$ hr, or at least about 2000 $g/m^2/24$ hr, or at least about 4000 $g/m^2/24$ hr, or at least about 7000 $g/m^2/24$ hr. The substrate layer of the device of the present invention may have a moisture vapour transmission rate of from about 2000 $g/m^2/24$ hr to about 7000 $g/m^2/24$ hr, or from about 3000 $g/m^2/24$ hr to about 6000 $g/m^2/24$ hr, or from about 3500 $g/m^2/24$ hr to about 5500 $g/m^2/24$ hr, or from about 4000 $g/m^2/24$ hr to about 5000 $g/m^2/24$ hr.

In yet further embodiments, the peel adhesive force of the laminate structure may be from about 10 N/2.5 cm to about 20 N/2.5 cm, or from about 12 N/2.5 cm to about 18 N/2.5 cm, or from about 14 N/2.5 cm to about 18 N/2.5 cm, or from about 15 N/2.5 cm to about 17 N/2.5 cm, or from about 16 N/2.5 cm to about 17 N/2.5 cm.

The fluid absorbance of the laminate structure may be from about 3 grams/10 $cm^2$/24 hours to about 6 grams/10 $cm^2$/24 hours, e.g. from about 4 grams/10 $cm^2$/24 hours to about 5 grams/10 $cm^2$/24 hours.

The total fluid handling of the device of the laminate structure may be from about 8 grams/10 $cm^2$/24 hours to about 12 grams/10 $cm^2$/24 hours, e.g. from about 9 grams/10 $cm^2$/24 hours to about 10 grams/10 $cm^2$/24 hours.

It will be understood that the aperture formed within the device of the present invention may be any suitable shape which is capable of expanding radially to accommodate a stoma, such as via the "stretch fit" mechanism as described herein. The aperture is capable of being expanded to be large enough to allow insertion of a given stoma such that the stoma extends through the device. In some embodiments, when the peripheral wall is in its pre-expanded state, the aperture may be substantially circular. As referred to herein, substantially circular may include oval. In embodiments, the aperture may be circular.

In some embodiments, the device may include one or more auxiliary layers. Such auxiliary layers may include at least one release liner to protect the adhesive layer of the device prior to use.

In a second aspect of the present invention is provided the use of an ostomy device according to any aspect or embodiment of the ostomy device described herein for contacting a stoma wherein the use includes providing the ostomy device, expanding the peripheral wall of the ostomy device in the plane of the laminate structure from the pre-expanded state to the expanded state to radially enlarge the aperture, inserting the stoma through the enlarged aperture and contacting the stoma with the peripheral wall. In another aspect there is a method of contacting a stoma with an ostomy device of the invention comprising providing an ostomy device of the present invention as defined herein, expanding the peripheral wall of the ostomy device in the plane of the laminate structure from the pre-expanded state to the expanded state to radially enlarge the aperture, inserting the stoma through the enlarged aperture and contacting the stoma with the peripheral wall.

In an embodiment, following insertion of the stoma into the enlarged aperture, the peripheral wall is contracted from the expanded state towards the pre-expanded state to cause the peripheral wall to contact the stoma.

In further embodiments, the contact between the peripheral wall and the stoma forms a seal between the peripheral wall and the stoma.

In embodiments, expanding the peripheral wall in the plane of the laminate structure from the pre-expanded state to the expanded state to radially enlarge the aperture may comprise a user applying a stretching force to the laminate structure toward the expanded state. In embodiments, the user may control the stretching force applied to the laminate structure to vary the extent of the aperture enlargement. Moreover, the user may maintain the stretching force during insertion of the stoma through the enlarged aperture to keep the aperture in an expanded state.

It will also be appreciated that the contracting of the peripheral wall from the expanded state towards the pre-expanded state to cause the peripheral wall to contact the stoma may include a user releasing the material, thus removing the stretching force mentioned above. In further embodiments, the contracting of the peripheral wall may occur under its own force once the user has released the stretching force.

Preferably, the diameter of the aperture in its pre-expanded state is smaller than the diameter of the stoma to which the device is applied. When the peripheral wall material is able to retract under its own force after the stretching force applied by the user has ceased, this feature will allow the peripheral wall to apply a force against the stomal skin (usually to form a liquid-tight seal) as the peripheral wall attempts to contract back toward its initial pre-expanded state but is impeded by the stoma.

A third aspect of the present invention relates to a kit of parts for preparing an ostomy collection device assembly, the kit including an ostomy device of the present invention for contacting a stoma and an ostomy pouch. In addition, the kit of parts may also include components, such as selected from, a sealing clip, cleaning set, belt (suitable for supporting an ostomy pouch), a barrier spray, an odor spray or odor drops, adhesive removal spray, wipe and closing plug. The ostomy pouch may be a one-piece pouch or multiple piece pouch, e.g. two piece pouch.

The device of the present invention may form part of a system including multiple pieces or components, for example, the device may form part of a two piece ostomy system or a kit of parts having an ostomy collection pouch.

In some embodiments the ostomy device comprises a laminate structure, the laminate structure comprising a substrate layer and an adhesive layer, an aperture formed through the laminate structure and defined by a peripheral wall, wherein the peripheral wall is operable to (i) expand in the plane of the laminate structure from a pre-expanded state to an expanded state to radially enlarge the aperture to allow insertion of the stoma through the aperture and (ii) contact the stoma (e.g. the base of the stoma), wherein once in its expanded state, the peripheral wall is further operable to contract from the expanded state towards its pre-expanded state to radially reduce the aperture and contact the stoma with the peripheral wall, wherein the contact between peripheral wall and the stoma forms a seal between the peripheral wall and the stoma, (e.g. the base of the stoma) the substrate layer comprising a polymer material (e.g. a polyurethane or polyethylene material, such as MEDI-FOL™ 3D), and the adhesive layer comprising a hydrocolloid (e.g. the exemplary hydrocolloid as defined below in Table 1b) and optionally wherein the overall thickness of the laminate structure is from about 0.1 mm to about 1.0 mm or, even more preferably, from about 0.5 mm to about 1.0 mm.

Ostomy devices of the present invention are suitable for use with ostomy collection pouches. The ostomy device of the present invention may suitably therefore include features that allow for mounting (i.e. securing or attaching) an ostomy collection pouch. The collection pouch, when in use, provides a means of collecting effluent or fluid output from the stoma.

In a further aspect there is provided a system comprising an ostomy device of the present invention as described herein and optionally an ostomy collection pouch.

DESCRIPTION OF THE FIGURES

The present invention will now be described with reference to the following non-limiting examples and figures, which show.

DETAILED DESCRIPTION OF THE INVENTION

Figure 1:
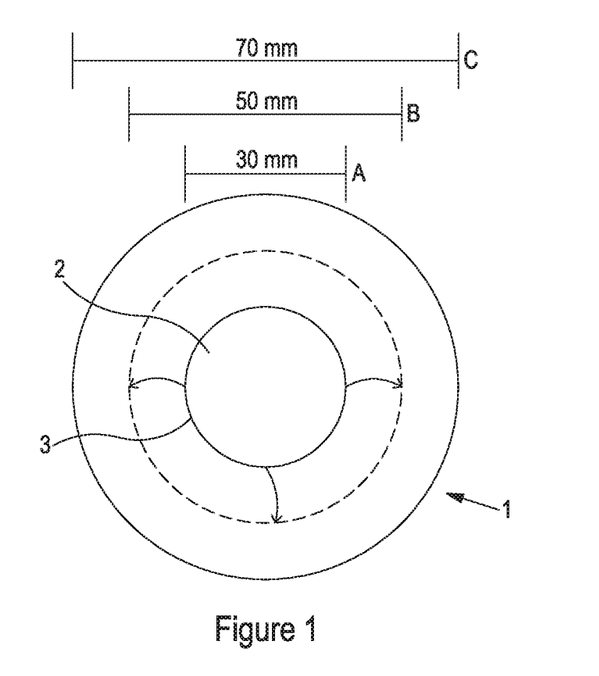
FIG. 1: A plan view of an ostomy device according to an embodiment of the invention shown in its pre-expanded state and in various expanded states (i.e. when a stretching force is applied by a user during application to a stoma to enlarge the aperture before insertion of a stoma has occurred).

Referring to FIG. 1, there is depicted an ostomy device 1, for application to a stoma (not shown) according to a preferred embodiment of the present invention. As described herein, the ostomy device 1 can vary in size or shape depending on the nature and dimensions of the stoma to which the device 1 is to be applied. In a preferred embodiment, the ostomy device 1 has a laminate structure, as described herein, including a substrate layer and adhesive layer. It can be seen in FIG. 1 that ostomy device 1 has an aperture 2 which is suitable for receiving a stoma, during use. The aperture 2 is defined by a peripheral wall 3 of the ostomy device 1. During application, the user increases the size of the aperture 2 by applying a stretching force (depicted by the arrows in FIG. 1) in the plane of the device 1. This stretching force causes the peripheral wall 3 to expand in a radial direction to cause radial enlargement of the aperture 2. The extent of the expansion of the peripheral wall 3 and enlargement of the aperture 2 can be varied by the user via control of the stretching force applied to the device 1. FIG. 1 shows the device in its pre-expanded state (A) before the user has applied a stretching force to the device. Also shown is the device in expanded states (B) and (C) wherein a stretching force is applied to the device 1 causing expansion of the peripheral wall 3 in the radial direction and thus causing radial enlarging of the aperture 2.

Figure 2:
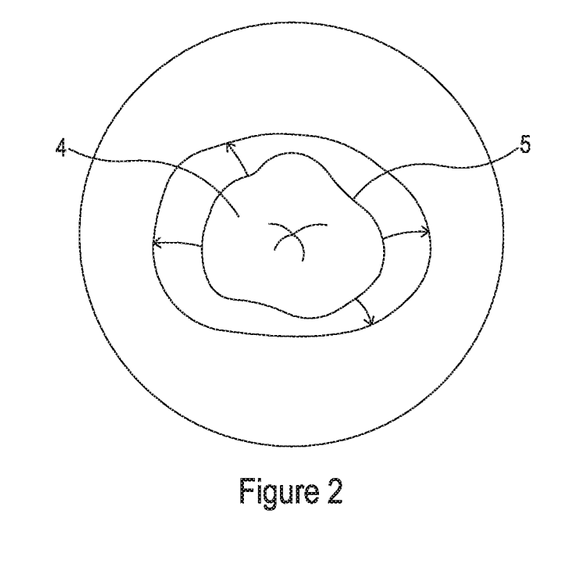
FIG. 2: A plan view of an ostomy device according to an embodiment of the invention shown in its expanded state (i.e. when a stretching force is applied by a user during application) with insertion of a stoma.

Referring now to FIG. 2, during application, the user may apply and maintain a stretching force to device 1 which allows an expanded state to be adopted. The user can ensure that the expanded state is suitable for insertion of a given stoma 4 by creating an aperture which has an enlarged diameter that is greater than the diameter of the stoma 4. When stoma 4 is inserted into aperture 2, it is preferred that no contact is made between the outer surface/wall 5 of the stoma 4 and the peripheral wall 3. This will prevent irritation and/or discomfort to the user whilst applying the device 1 to the stoma 4.

Figure 3:
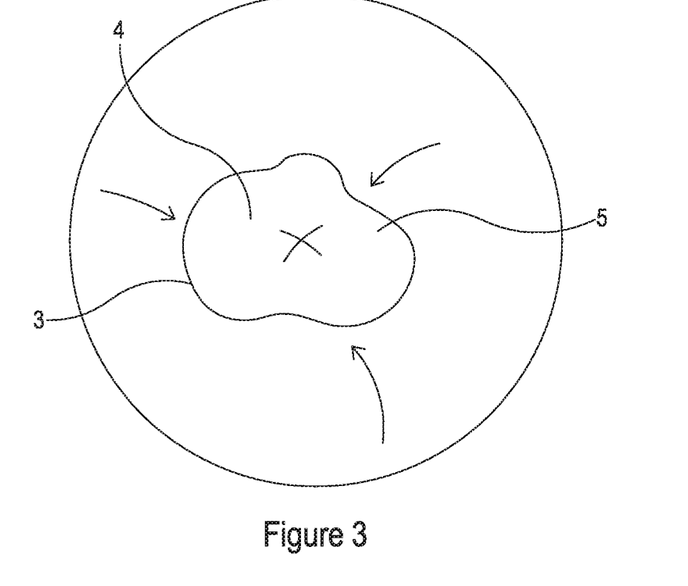
FIG. 3: A plan view of an ostomy device according to an embodiment of the invention shown in its sealed state (i.e. applied to a stoma to form a seal).

With reference to FIG. 3, once the user has inserted stoma 4 into the expanded aperture 2, the user may then release the stretching force applied to the device 1. In this example, the material of the device is able to retract under its own force once the user has released the tension. This causes the peripheral wall 3 to radially contract (as indicated by the arrows in FIG. 3) and contact the outer wall 5 of the stoma 4, preferably forming a seal with the outer wall 5 of the stoma 4. However, in alternative embodiments, the material may not retract under its own force. As shown in FIG. 3, when the seal is preferably formed, the peripheral wall 3 contracts and conforms to the anatomy or profile of the stoma outer wall 5. In order to ensure that a secure seal is formed between the peripheral wall 3 of the device and the stoma 4 (i.e. no gaps exist between the peripheral wall 3 and the outer wall 5 of the stoma 4 through which bodily fluid may pass), it is preferred that the user ensure that the diameter of the aperture 2 in its pre-expanded state is smaller than the diameter of the stoma to which the device is applied. This will enable the device to better form a seal as the device material retracts back towards its pre-expended state but is impeded by the stoma, and thus exerts a force on the stoma. By virtue of this retractiretracts back towards its pre-expended state but is impeded by the stoma, and thus exerts a force on the stoma. By virtue of this reretracts back towards its pre-expended state but is impeded by the stoma, and thus exerts a force on the stoma. By virtue of this retraction mechanism, this force is typically much less than the force exerted by certain prior art devices which do not operate in the same way.

Figure 4:
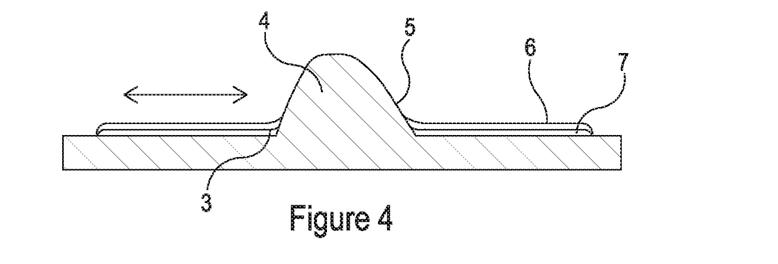
FIG. 4: A side or cross-sectional view of an ostomy device according to an embodiment of the invention shown in its sealed state.

FIG. 4 provides a cross-sectional view of an ostomy device 1 shown in its sealed state. The laminate structure of the device 1 is shown in FIG. 4 wherein the adhesive layer 7 is adhered to the peristomal skin and supports a substrate layer 6. The peripheral wall 3 of the device and the outer wall 5 of the stoma are also shown.

As illustrated in FIGS. 1-4, the device of the present invention may operate using a "stretch-fit" mechanism which allows the user to easily apply the ostomy device of the present invention to a stoma. Unlike known conventional skin barrier devices, the "stretch-fit" mechanism achieved by the device of the present invention is easy to apply. This fit mechanism also allows for a less forceful contact with the stoma, which may prevent leakages whilst avoiding discomfort for the user, thus protecting the peristomal skin.

Preparation of the Ostomy Device

The ostomy device of the present invention may be suitably manufactured according to conventional manufacturing methods. An exemplary method of manufacturing an ostomy device of the present invention is provided below:
1. A suitable hydrocolloid roll stock (e.g. sodium carboxymethylcellulose, polysaccharides and pectin containing hydrocolloid roll stocks) is mixed at a temperature of 80° C.-120° C. to form a hydrocolloid dope.
2. The hydrocolloid dope is then shaped into hydrocolloid logs for downstream processing.
3. The hydrocolloid logs are then extruded through a heated die with a set aperture at 90° C.-120° C. onto a suitable carrier liner (e.g. paper or film) to form an hydrocolloid sheet.
4. A suitable substrate layer (e.g. a polyurethane backing film) is then laid on top of the extruded hydrocolloid sheet.
5. The hydrocolloid sheet and the substrate layer are then laminated using nip rollers to provide a laminate material.
6. The laminate material can then be wound into a roll stock before then being cut to the required size and dimensions to form an ostomy device of the present invention.

Suitable hydrocolloid roll stock materials and or substrate layers are readily available and may be purchased or prepared using conventional methods.

Experimental Tests

A series of tests were performed to measure the performance of an exemplary ostomy device of the present invention and a number of commercially available mouldable ostomy devices, the details of which are set out below. All test methods and procedures used to obtain the test data are provided herein and, unless specified otherwise, are known to the person skilled in the art.

Product details of the commercially available mouldable ostomy devices which were tested are provided in Table 1a below.

TABLE 1a

| Product Name | Product Reference Number |
| --- | --- |
| ConvaTec ™ Esteem (stoma range 30-40 mm) | 413516 |
| Coloplast ™ Brava Ring Mouldable | 12030 |
| Hollister ™ Adapt (largest diameter 48 mm) | 8815 |
| Eakin ™ Cohesive Seals (largest diameter 98 mm) | 839001 |

The exemplary ostomy device of the present invention used for the purposes of the following tests is referred to herein as the "AMS Ostomy Device (OD)". AMS OD may be manufactured using the exemplary manufacturing method as described above using the hydrocolloid specified in Table 1 b below and substrate film, MEDIFOL™ 3D. Physical characteristics and performance characteristics of the resulting AMS OD device according to the invention are described below in comparison to prior art devices. The hydrocolloid may be manufactured and formulated using techniques and procedures known to the person skilled in the art. One example technique for manufacturing hydrocolloids involves mixing the hydrocolloid ingredients using a Z-blade mixer at a suitable temperature, such as 80° C.-120° C., preferably 90° C.

An exemplary hydrocolloid for use in embodiments of the invention is described in Table 1 b below. This hydrocolloid composition was the composition used in the tested "AMS Ostomy Device (OD)" described herein.

TABLE 1b

| Hydrocolloid | Component Amount (wt %) |
| --- | --- |
| Polyisobutylene | 28.36 |
| Carboxymethylcellulose | 29.63 |
| Poly(styrene-butadiene-styrene) Block Copolymer | 16.29 |
| Hydrocarbon Resin | 10.40 |
| Purified Powdered Cellulose, Flock | 8.44 |
| Pectin | 6.35 |
| Other ingredients (including preservative and liquid phase oil) | 0.53 |

A series of tests were performed on AMS OD and the resulting pH, Total Fluid Handling (TFH), Moisture Vapour Transmission Rate (MTVR), Fluid Absorbance and Peel/Adhesion Force data can be found presented in Table 2 below.

TABLE 2

| | Batch 1 | Batch 2 | Batch 3 | Batch 4 | Average |
| --- | --- | --- | --- | --- | --- |
| pH | 6.67 | 6.71 | 6.60 | 6.68 | 6.66 |
| Total Fluid Handling (g/10 cm$^2$/24 hr) | 9.224 | 9.022 | 8.723 | 9.976 | 9.24 |
| Moisture Vapour Transmission Rate (g/m$^2$/24 hr) | 4079 | 4399 | 3424 | 6717 | 4655 |
| Fluid absorbance (g/10 cm$^2$/24 hr) | 5.144 | 4.623 | 5.299 | 3.259 | 4.581 |
| Peel/Adhesion Force (N/2.5 cm) | 16.916 | 17.824 | 14.817 | — | 16.519 |

For each of the test performed on batch samples 1 to 4 as shown in Table 2, 10 data points were taken before being averaged to provide the batch data presented in batch 1-4 columns. The average column (shown at the far right of the Table 2) is an average value of the data provided in the batch 1-4 columns provided.

pH Measurements of AMS OD

The method used to assess the pH of the AMS OD is aligned with British Pharmacopoeia Appendix V A120 L.

A sample of the AMS OD device (0.3 g) is measured using a calibrated analytical balance and transferred into a suitable container. This is followed by the addition of purified water (30 ml) before the mixture is shaken from 30 seconds using a vortex. The solution is decanted into clean containers and the pH is measured using a calibrated pH meter and probe.

A neutral pH was observed for the AMS OD which is ideal for devices applied onto the surface of the skin.

Total Fluid Handling of AMS OD

The Total Fluid Handling (TFH), Moisture Vapour Transmission Rate (MTVR) and Fluid Absorbance data presented in Table 2 was obtained using a method which is aligned with ISO 13726-1:2002 *Test Methods for Primary Wound Dressings—Part 1: Aspects of Absorbent section* 3.3 *Fluid Handling Capacity*. The procedure requires a circle of the AMS OD to be cut to have a 55 cm diameter. The circle of AMS OD was then attached to the flange of a Paddington Cup (a hollow cup with a 10 cm² cross section) and secured in place with a retaining ring (e.g. screw top). The weight of the AMS OD and the Paddington Cup is measured (W1) and recorded using a calibrated balance. Then 20 ml of Solution A is added to the Paddington Cup and the screw top applied. Solution A is a standard test solution used in wound care contains 142 milimoles of sodium ions and 2.5 milimoles of calcium ions dissolved in distilled water (made as per ISO 13726-1:2002). The Paddington Cup is positioned such that the adhesive side of the AMS OD sample is in contact with Solution A. The Paddington Cup is then weighed again (W2) and the weight is recorded. The Paddington Cup is placed into a 37° C. environmental chamber for 24 hours. Upon removal, the Paddington Cup is left to stand for 30 minutes and the weight recorded (W3). The solution is drained and the Paddington Cup is inverted for 15 minutes before having the weight of the cup measured and recorded for the final time (W4).

The Moisture Vapour Transmission Rate (MVTR) and Fluid Absorbance for the AMS OD sample was calculated according to the following.

MVTR=$W2-W3 \times 1000$ (Units: g/m²/24 hrs)

Fluid Absorbance=$W4-W1$ (Units: g/10 cm²/24 hrs)

The total fluid handling is the sum of MVTR and Fluid absorbance values. The MVTR indicates the breathability of the device, which is an important factor for the AMS OD as it will usually be secured to and contact with the peristomal skin of a user when in operation. The MTVR of the AMS OD was found to be surprisingly high. This shows that the AMS OD possesses excellent breathability properties which would allow for the safe and comfortable application of the device to a stoma. Lower MVTR values would indicate poorer breathability, rendering the device more prone to impair the intact skin.

It has also been observed that upon hydration/full saturation, the exemplary AMS OD swelled to form a soft seal and remained integral under compression. This effect is advantageous when compared to other devices (e.g. Coloplast Brava Ring Mouldable) since the other devices tend to swell upon hydration but disintegrate upon compression. This would make it more difficult and messier for the user to change the prior art devices (e.g. adhesive wipes are required) and may allow stomal output to come into contact with the peristomal skin which can cause redness, soreness and irritation to the user. The AMS OD thus avoids these negative effects.

Peel Adhesion of AMS OD

The peel adhesion data was obtained using a method which is aligned with ASTM D6282-11.

A sample of the AMS OD was cut to 25 mm×100 mm using a cutting press and die. The sample was tape wrapped around one end to form a tab for use with the tensometer. A stainless steel plate was then cleaned with isopropyl alcohol wipes or acetone. The release liner of the cut sample is removed and the sample is applied to the stainless steel plate. The sample and plate were placed on a calibrated 'roll down' machine at a speed of 12 inch/min. The stainless steel plate was mounted onto the test rig of a tensometer (Zwick model) so that the tab created is secured in the upper jaw at a 90 degree angle. The upper jaw was moved up, peeling the adhesive from the stainless steel plate at a rate of 254 mm/min. The maximum force and the average force are measured by the tensometer in Newtons.

Thickness Tests

TABLE 3

| Product Name | Thickness of device with auxiliary layers (mm) | Thickness of auxiliary layers (mm) | Thickness of device (mm) |
|---|---|---|---|
| ConvaTec Esteem+ mouldable | 18.12 | 0.11 | 18.01 |
| Coloplast Brava Ring Moudable | 20.47 | 0.047 | 20.42 |
| Hollister Adapt | 22.96 | 0.050 | 22.91 |
| Eakin Cohesive Seals | 25.91 | 0.161 | 25.75 |
| AMS OD | — | — | 0.70 |

The thickness data presented in Table 3 for the commercially available mouldable ostomy devices and the AMS OD was obtained using the following method. The device is first removed from its primary packaging. The total thickness of the device including any auxiliary layers (e.g. release liners) is then measured using a calibrated digital calliper and the measurement is recorded at three points on the device. The measurement is taken with release liners on in order to avoid the equipment becoming tacky. This also reduces the risk of the calliper compressing the adhesive and thus giving a false lower reading. The release liners are then removed and measured using the same calliper at three points on the release liner. The final thickness of the device is calculated as the average thickness of the device (as measured with the release liners) minus the average thickness of the release liners.

It can be seen that the average thickness of the exemplified AMS OD is significantly less than that of the commercially available mouldable ostomy devices. The thickness of the AMS OD is important in providing the device of the present invention with its desirable flexibility and strength. Moreover, the thickness of the device plays a major role in the device achieving excellent conformability properties and allows for the device to adapt to the contours of a user's body when in use. Conformability data for the AMS OD and commercially available ostomy devices is provided and discussed in more detail below. In addition, the thickness of the device of the present invention is crucial in achieving the gentle fit against a stoma wall in use.

Conformability Tests

Conformability tests were performed on the ConvaTec Esteem+ mouldable device, Eakin Cohesive Seals and the AMS OD. The conformability data presented in Tables 4-6 below was obtained using the following method. The resulting data is shown in Table 4 for the ConvaTec Esteem+ mouldable device, in Table 5 for the Eakin Cohesive Seals and in Table 6 for the AMS OD.

The method used to obtain the conformability presented herein is aligned with ISO EN 13426-4:2003 *Test methods for primary wound dressings—Part 4: Conformability*. This method sees a sample of the device cut in to a rectangular strip having a width of 2.5 cm. The strip then has two pieces of tape wrapped around either of its ends, which are approximately 100 mm apart. The release liners of the device are then removed, if necessary, and the product is left to relax for a minimum of 300 seconds. The distance between the two pieces of tape is measured using a digital calliper and recorded as L1. The sample is then mounted into a tensometer (AMS use Zwick Roell machine) and clamped into the jaws of the machine via the taped ends. The sample is extended by 20% at a rate of 300 mm/min and is held at the maximum extension for 60 seconds. The force to extend by 20% is recorded by the tensometer as the Fmax/Maximum force (Newtons). After 60 seconds the sample is released from the jaws of the tensometer and left to relax for a further 300 seconds. The distance between the taped ends is measured again using the digital callipers and recorded as L2. Each experiment was repeated five times to provide samples number 1-5 in the tables below.

Extensibility is defined as the force required to stretch a wound dressing sample to a known extension. To calculate the extensibility the Fmax is divided by 2.5 cm.

Permanent set is defined as the increase in length of a sample after the stretching and relaxing expressed as a percentage of the original length. The permanent set is calculated as follows:

$$\text{Permanent Set (\%)} = ((L2 - L1)/L1) \times 100$$

Conformability is an important factor for medical devices that are in contact with the skin as the higher the conformability the better the ability of the device to adapt to the shape and movement of the body. The measurement of the permanent set provides an assessment of the memory of a device and ability of a device to contract. The force required to stretch or mould the device is also represented by the Fmax.

TABLE 4

ConvaTec Esteem + mouldable device

| Nr | Initial length (L1) mm | Final length (L2) mm | Max force (Fmax) N | | Extensibility N/cm | Permanent Set % |
|---|---|---|---|---|---|---|
| | A | B | C | D | E | F | G |
| 1 | 40.75 | 41.0 | 41.98 | 42 | 9.9 | 3.96 | 2.44 |
| 2 | 44.26 | 44.5 | 44.80 | 45 | 9.4 | 3.76 | 1.12 |
| 3 | 43.94 | 44.0 | 44.05 | 44 | 8.4 | 3.36 | 0.00 |
| 4 | 44.05 | 44.0 | 46.54 | 46.5 | 8.3 | 3.32 | 5.68 |
| 5 | 45.65 | 45.5 | 47.93 | 48 | 8.1 | 3.24 | 5.49 |
| | | | | | Mean | 3.53 | 2.95 |
| | | | | | StDev | 0.31 | 2.56 |

TABLE 5

Table 5 for the Eakin Cohesive Seals

| Nr | Initial length (L1) mm | Final length (L2) mm | Max force (Fmax) N | | Extensibility N/cm | Permanent Set % |
|---|---|---|---|---|---|---|
| | A | B | C | D | E | F | G |
| 1 | 55.86 | 56 | 71.29 | 71.5 | 2.8 | 1.12 | 27.68 |
| 2 | 65.29 | 65.5 | 79.85 | 80 | 2.9 | 1.16 | 22.14 |
| 3 | 58.93 | 59 | 73.68 | 73.5 | 2.5 | 1.00 | 24.58 |
| 4 | 59.12 | 59 | 77.07 | 77 | 2.7 | 1.08 | 30.51 |
| 5 | 64.64 | 64.5 | 77.46 | 77.5 | 2.6 | 1.04 | 20.16 |
| | | | | | Mean | 1.08 | 25.01 |
| | | | | | StDev | 0.06 | 4.16 |

TABLE 6

AMS OD according to the invention

| Nr | Initial length (L1) mm | Final length (L2) mm | Max force (Fmax) N | | Extensibility N/cm | Permanent Set % |
|---|---|---|---|---|---|---|
| | A | B | C | D | E | F | G |
| 1 | 84.83 | 85 | 85.83 | 86 | 13.6 | 5.44 | 1.18 |
| 2 | 93.23 | 93 | 94.37 | 94.5 | 13.1 | 5.24 | 1.61 |
| 3 | 92.55 | 92.5 | 93.82 | 94 | 13 | 5.2 | 1.62 |

TABLE 6-continued

AMS OD according to the invention

| Nr | Initial length (L1) mm | Final length (L2) mm | Max force (Fmax) N | | Extensibility N/cm | Permanent Set % |
|---|---|---|---|---|---|---|
| | A | B | C | D | E | F | G |
| 4 | 92.64 | 92.5 | 93.9 | 94 | 13 | 5.2 | 1.62 |
| 5 | 92.6 | 92.5 | 94.24 | 94 | 12.7 | 5.08 | 1.62 |
| | | | | | Mean | 5.23 | 1.53 |
| | | | | | StDev | 0.13 | 0.20 |

As can be seen from the data in Table 6 above, an AMS OD of the present invention demonstrated higher Fmax and extensibility values as compared to the comparative ConvaTec Esteem+ moudlable and Eakin Cohesive Seals devices. Moreover, the permanent set value obtained for the AMS OD of the present invention, is significantly lower than the comparator devices. This illustrates that the exemplified device of present invention showed a greater tendency to return to its original shape after a stretching force was applied. This indicates that if the user were to apply the device of the present invention to a stoma (as described herein with reference to FIGS. 1-4), the relative ease of stretching and increased tendency to return to its original state (i.e. pre-expanded or resting state) would make the device of the invention more able to form a secure seal between the peripheral wall defining the aperture of the device and the wall of the stoma once the device has contracted.

As mentioned above, the "stretch-fit" mechanism achieved by the device of the present invention is generally easy to apply and is able to form a seal with the wall of the stoma (e.g. to prevent fluid leakage from the stoma contacting the skin) without imparting excessive compression forces on the stoma. The exemplary device of the invention described above possesses exceptional mechanical strength and stretching characteristics (demonstrated by the Fmax and extensibility values described above) as well as excellent contraction and sealing properties (demonstrated by the permanent set values described above). In addition to these characteristics, the present inventors have also been able to advantageously achieve a desirable rebounding effect on the stoma by the device. This can be attributed to the novel mechanism of action of the device (typically delivered by virtue of a relatively thin laminate structure), and may be accentuated by the choice of laminate material.

It will be appreciated that numerous modifications to the above described ostomy device and use may be made without departing from the spirit and scope of the invention, for instance, the scope of the invention as defined in the appended claims. Moreover, any one or more of the above described embodiments could be combined with one or more features of the other embodiments and all such combinations are intended within the present disclosure.

Optional and/or preferred features may be used in other combinations beyond those explicitly described herein and optional and/or preferred features described in relation to one aspect of the invention may also be present in another aspect of the invention, where appropriate.

The described and illustrated embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," or "at least one," are used to preface a feature there is no intention to limit the claim to only one such feature unless specifically stated to the contrary in the claim.

The invention claimed is:

1. An ostomy device for contacting a stoma comprising:
   a laminate structure comprising a substrate layer and an adhesive layer; and
   an aperture formed through the laminate structure and defined by a peripheral wall;
   wherein the laminate structure has (i) an extensibility in a range of about 1 newton per centimeter (N/cm) to about 10 N/cm and (ii) a permanent set value of less than or equal to about 5%;
   wherein the peripheral wall is configured to:
   expand in a plane of the laminate structure from a pre-expanded state to an expanded state to radially enlarge the aperture to allow insertion of the stoma through the aperture and, once in its expanded state, the peripheral wall is further operable to contract from the expanded state towards its pre-expanded state to radially reduce the aperture and contact the stoma with the peripheral wall, wherein the contact between the peripheral wall and the stoma forms a seal between the peripheral wall and the stoma.

2. The ostomy device according to claim 1, wherein the substrate layer comprises a foam and/or film.

3. The ostomy device according to claim 1, wherein the substrate layer comprises a polymer.

4. The ostomy device according to claim 3, wherein the polymer comprises a polyurethane or polyethylene.

5. The ostomy device according to claim 1, wherein the adhesive layer comprises a hydrocolloid, a silicone adhesive, an acrylic adhesive, a polyurethane adhesive, or any combination of two or more thereof.

6. The ostomy device according to claim 5, wherein the hydrocolloid comprises sodium carboxymethylcellulose, polysaccharides and pectin.

7. The ostomy device according to claim 1, wherein a thickness of the substrate layer is from about 0.005 mm to about 0.1 mm.

8. The ostomy device according to claim 7, wherein the thickness of the substrate layer is from about 0.005 mm to about 0.05 mm.

9. The ostomy device according to claim 1, wherein a thickness of the adhesive layer is from about 0.1 mm to about 10 mm.

10. The ostomy device according to claim 9, wherein a thickness of the adhesive layer is from about 0.1 mm to about 5 mm, 0.2 mm to about 4.0 mm or from about 0.5 mm to about 3.0 mm.

11. The ostomy device according to claim 1, wherein:
    (a) an overall thickness of the laminate structure is from about 0.1 mm to about 10 mm, 0.2 mm to about 5.0 mm or about 0.5 mm to about 1.0 mm; or
    (b) the laminate structure has an extensibility of from about 3 N/cm to about 8 N/cm or from about 5 N/cm to about 6 N/cm; or
    (c) the laminate structure has a permanent set (%) of less than or equal to about 2%; or
    (d) the substrate layer has a moisture vapour transmission rate of at least about 500 $g/m^2/24$ hr, or at least about 2000 $g/m^2/24$ hr, or at least about 4000 $g/m^2/24$ hr, or from about 4000 $g/m^2/24$ hr to about 5000 $g/m^2/24$ hr; or
    (e) a peel adhesive force of the laminate structure is from about 10N/2.5 cm to about 20N/2.5 cm or from about 12N/2.5 cm to about 18N/2.5 cm; or
    (f) a fluid absorbance of the laminate structure is from about 3 grams/10 $cm^2/24$ hours to about 6 grams/10 $cm^2/24$ hours, or from about 4 grams/10 $cm^2/24$ hours to about 5 grams/10 $cm^2/24$ hours.

12. The ostomy device according to claim 1, wherein a total fluid handling of the laminate structure is from about 8 grams/10 cm2/24 hours to about 12 grams/10 $cm^2/24$ hours, or from about 9 grams/10 $cm^2/24$ hours to about 10 grams/10 $cm^2/24$ hours.

13. The ostomy device according to claim 1, wherein when the peripheral wall is in its pre-expanded state, the aperture is substantially circular.

14. The ostomy device according to claim 1, further comprising a release liner to protect the adhesive layer prior to use.

15. A method for contacting a stoma with the ostomy device of claim 1, the method comprising:
    expanding the peripheral wall in the plane of the laminate structure of the ostomy device from the pre-expanded state to the expanded state to radially enlarge the aperture;
    inserting the stoma through the enlarged aperture; and
    contacting the stoma with the peripheral wall.

16. The method according to claim 15 wherein, following insertion of the stoma into the enlarged aperture, the peripheral wall is contracted from the expanded state towards the pre-expanded state to cause the peripheral wall to contact the stoma.

17. The method according to claim 15 wherein the contact between the peripheral wall and the stoma forms a seal between the peripheral wall and the stoma.

18. A kit of parts for preparing an ostomy assembly, the kit comprising:
    an ostomy device for contacting a stoma as defined in claim 1; and
    an ostomy pouch capable of engaging the ostomy device.

19. An ostomy device for contacting a stoma comprising:
    a laminate structure including a substrate layer and an adhesive layer; and
    an aperture formed through the laminate structure and defined by a peripheral wall;
    wherein the laminate structure has (i) an extensibility in a range of about 1 newton per centimeter to about 10 newtons per centimeter and (ii) a permanent set value of less than or equal to about 5%; and
    wherein the aperture is configured to allow insertion of the stoma through the aperture.

20. The ostomy device of claim 19, wherein the laminate structure has a fluid absorbance in a range of about 5 grams per 10 centimeters squared per 24 hours (g/10 $cm^2/24$ h).

* * * * *